United States Patent [19]

Tonomura et al.

[11] 4,229,543
[45] Oct. 21, 1980

[54] PROCESS FOR CULTURING METHANOL-UTILIZING YEASTS

[75] Inventors: Kenzo Tonomura, Chiba; Teizi Urakami, Niigata, both of Japan

[73] Assignees: Agency of Industrial Science & Technology; Ministry of International Trade and Industry; Mitsubishi Gas Chemical Company, Inc., all of Tokyo, Japan

[21] Appl. No.: 941,641

[22] Filed: Sep. 12, 1978

Related U.S. Application Data

[63] Continuation of Ser. No. 638,264, Dec. 8, 1975, abandoned, which is a continuation of Ser. No. 468,866, May 10, 1974, abandoned.

[30] Foreign Application Priority Data

May 11, 1973 [JP] Japan .................. 48-53005

[51] Int. Cl.$^2$ .................. C12N 1/36; C12N 1/32; C12N 1/16
[52] U.S. Cl. .................. 435/245; 435/247; 435/255
[58] Field of Search .................. 195/49, 82, 86, 93, 195/99, 79, 112, 115; 435/247, 255, 813, 921, 940, 944, 930, 245

[56] References Cited

FOREIGN PATENT DOCUMENTS 2006235 12/1969 France .................. 195/49
2070840 9/1971 France .................. 195/49
1210770 10/1970 United Kingdom .................. 195/49

OTHER PUBLICATIONS

Morris, "Yeast Growth", *The Chemistry and Biology of Yeast*, Cook, ed., Academic Press, N. Y., pp. 256–264 (1958).
Oki et al., "New Yeasts Capable of Assimilating Methanol", *Chem. Absts.*, vol. 78, p. 224, (1973) Abs. No. 26258a.
Stanier et al., *The Microbial World*, Prentice-Hall, Inc., Englewood Cliffs, 3rd Ed. (1970), pp. 306–316.

*Primary Examiner*—Thomas G. Wiseman
*Attorney, Agent, or Firm*—Birch, Stewart, Kolasch & Birch

[57] ABSTRACT

A process for culturing methanol-utilizing yeasts, wherein a methanol-utilizing yeast is cultured in a medium containing methanol as a main carbon source, using as seeds yeast cells obtained by culturing the yeast in a culture liquor containing methanol at a concentration higher than 0.1 wt. % and not more than 6 wt. %.

10 Claims, No Drawings

PROCESS FOR CULTURING METHANOL-UTILIZING YEASTS

This application is a continuation of copending application Ser. No. 638,264, abandon, filed on Dec. 8, 1975, which is a continuation of Ser. No. 468,866, filed on May 10, 1974 abandon.

This invention relates to a process for the seed culture of a methanol-utilizing yeast in a medium containing methanol as a main carbon source.

As processes for culturing methanol-utilizing yeasts in a medium containing methanol as a main carbon source, there have already been proposed a process in which the cultivation is completed with the amount of methanol provided initially without supplementation of fresh methanol, and a process in which methanol is initially used at a low concentration and fresh methanol is successively supplemented in an amount corresponding to the amount of consumed methanol.

Commercial scale cultivation of microorganisms is carried out either in a batch-wise or continuous manner. In case a methanol-utilizing yeast is cultured in a batch-wise manner in a medium containing methanol as a main carbon soure, there is required a growth induction period (the period required for the yeast from inoculation thereof into the medium to active exponential proliferation thereof) of such a long period as ten hours, in general. This not only lowers the utilization degree of the apparatus used, but also brings about such disadvantages that the amount of methanol lost due to its inclusion in the waste gas at the time of aeorbic stirring of the culture is increased so as to decrease the yield of resulting cells based on the amount of starting methanol. Even in the case where the aforesaid yeast is cultured in a continuous manner, batch-wise pre-cultivation in, for example, a culture liquor medium should be conducted 2 to 3 times before reaching a stationary state. In said batch-wise pre-cultivation also, the same disadvantages as above are necessarily brought about.

An object of the present invention is to provide a process for culturing a methanol-utilizing yeast with commercial advantages by shortening the growth induction period of the yeast at the time of batch-wise cultivation thereof, or of batch-wise pre-cultivation for continuous cultivation thereof.

According to the present invention, a yeast is pre-cultured in a culture liquor containing methanol as a main carbon source at a concentration higher than 0.1 wt% and not more than 6 wt% and additionally containing nutrient sources necessary for the growth of said yeast, thereby obtaining a seed yeast. The thus obtained seed yeast is then cultured in a batch-wise or continuous manner in a culture medium containing methanol as a main carbon source and additionally containing other nutrient sources, which may be the same as or different from those in the said seed culture medium.

The seed culture according to the present invention is explained below.

Medium:

The seed culture medium contains methanol as a main carbon source and additionally contains other nutrient sources, e.g. nitrogen sources, etc.

As the nitrogen sources, there are used inorganic nitrogen compounds such as, for example, ammonium salts and nitrates. It is also possible to use organic nitrogen-containing substances such as urea, corn steep liquor, casein, yeast extract and meat extract. In addition thereto, inorganic salts such as calcium salts, magnesium salts, potassium salts, phosphates, manganese salts, zinc salts, iron salts and copper salts, and, if necessary, substances necessarily required for growth, such as vitamins and amino acids, or growth promotors, may be added to the medium. If the concentration of methanol in the medium is 0.1 wt% or less, the aforesaid growth induction period is still several hours to serveral dozen hours. If the methanol concentration becomes substantially 0%, the growth induction period becomes a long period such as 17 to 20 hours. On the other hand, if the methanol concentration is higher than 6 wt%, the yeast itself, which is used as a seed yeast, is inhibited in growth and propagation. Among the above-mentioned nutriments, at least one nutriment except methanol may be decreased in amount. The extent of decrease in amount of the nutriment may previously be decided experimentally or known experimentally by examining whether or not the methanol concentration in the culture liquor becomes higher than 0.1 wt% and not more than 6 wt% at the time when said nutriment is all spent from the culture liquor.

Yeast:

The yeast may be any yeast so far as it has a methanol-utilizing property, and is properly selected according to the fermentation product desired.

Culturing:

Culturing is effected at a temperature of 20° to 45° C. and under a pH of 2 to 8, depending on the yeast employed. The period for culturing varies depending on the yeast, composition of medium, conditions for culturing and the fermentation product desired.

The seed yeast may be cultured according to any of the batch-wise cultivation procedures or continuous cultivation.

In the case of batch-wise cultivation, the methanol concentration in the culture liquor decreases with lapse of time, unless fresh methanol is supplemented in an amount corresponding to the amount of consumed methanol. In the case of continuous cultivation, the yeast may be cultured while maintaining the methanol concentration in the culture liquor at a definite concentration within the aforesaid range. Alternatively, the yeast may be cultured while varying the methanol concentration, e.g. while decreasing the methanol concentration with lapse of time. It is also possible to culture the yeast in a so-called complete medium containing a sufficient amount of the nutrient sources except methanol, while analysing the methanol content and confirming that the methanol concentration is kept within the aforesaid range. Both in batch-wise cultivation and continuous cultivation, the methanol concentration can be maintained in the aforesaid range by controlling the cultivation period or average residence time, the cultivation temperature, the cultivation pH and/or the concentration of oxygen in the culture liquor. The seed yeast is used as it is, i.e. without separation from the culture liquor, or used after separation from the culture liquor. From the ease of operation and from the smaller danger of contamination, the seed yeast is preferably used without separation from the culture liquor.

In the present invention, the cultivation period of the yeast to be used as a seed yeast means a period ranging from inoculation of the yeast at a certain stage to inoculation of said yeast as a seed yeast for cultivation at the subsequent stage. Accordingly, the methanol concentration in the culture liquor containing said seed yeast which is immediately before or at the time of inoculation at the subsequent stage should also be kept within the aforesaid range, though this is a matter of course.

The growth phase of the seed yeast itself is not particularly limited. That is, the yeast in a growth phase at any of the growth induction phase, logarithmic growth phase, stationary phase or extinction phase may be used as a seed yeast. From such viewpoint that the growth induction period is to be shortened as far as possible, however, it is preferable to use the yeast at the logarithmic growth phase or stationary phase as a seed yeast.

The process of the present invention is applicable not only to the production of cells as nucleic acids, vitamins, proteins, coenzymes and/or liquid sources, but also to the production of metabolic substances outside the cells.

The present invention is illustrated in more detail below with reference to examples.

EXAMPLE 1

3 Grams of $(HH_4)_2SO_4$, 4 g. of $KH_2FO_4$, C.4 g. of $MgSO_4.7H_2O$, 0.2 mg. of $FeSO_4.7H_2O$, 5 mg. of $CaCl_2.2H_2O$, 0.5 mg. of $MnSO_4.4H_2O$, 0.5 mg. of $ZnSO_4.7H_2O$, 4 µg. of biotin, 200 µg. of thiamine hydrochloride and 10 g. of methanol were dissolved in one liter of water to prepare a medium having a pH of 4.7. 200 Milliliters of the thus preapared medium was charged into a 1,000-ml Erlenmeyer flask. Subsequently, a yeast *Candida alcomigas* Ya-23 (FERM P 1973) (NRRL Y-8023) was inoculated in the medium, and subjected to seed culture at 30° C. by use of a rotary shaker. No methanol was supplemented during the period of said seed culture.

The methanol concentration in the cultire liquor decreased with growth of the yeast and with lapse of time. The yeasts at methanol concentrations in the culture liquor of (A) 0.6 wt%, (B) 0.4 wt%, (C) 0.2 wt%, (D) 0.1 wt%, (E) 0.05 wt% and (F) 0.00 wt%, respectively, were used as seed yeasts.

Each of the seed yeasts was inoculated into a 3-liter jar fermentor containing 1 liter of the same medium as above, so that the seed yeast concentration reached an optical density at 610 mµ of 0.05 (The photo-cell used in this example had a liquid layer of 10 mm in thickness. The same in Examples 2 and 3.). At the time of inoculation, the methanol concentration in each of the culture liquors containing the seed yeast was kept the same as above. The seed yeast was subjected to batch-wise cultivation while introducing air ahd while adding aqueous ammonia so that the initial pH of the culture liquor and the pH thereof during the cultivation became 4.7.

Growth induction periods, required in the case where the said seed yeasts were used, were measured to obtain the results as shown in Table 1.

TABLE 1

| Growth induction periods required in the case where various seed yeasts were used | | |
|---|---|---|
| Cultivation period of seed yeast (hrs.) | Methanol concentration in the culture liquor at the time of inoculation (wt %) | Growth induction period (hrs.) |
| A 45 | 0.6 | 3.0 |
| B 50 | 0.4 | 4.0 |
| C 56 | 0.2 | 6.0 |
| D 58 | 0.1 | 15.0 |
| E 60 | 0.05 | 15.0 |
| F 65 | 0.00 | 17.0 |

When the yeast pre-cultured in the culture liquor having a methanol concentration higher than 0.1 wt% and not more than 6 wt% was used as the seed yeast, the growth induction period became 6 hours or less. The period is less than one-half the period required in the case where the yeast pre-cultured in the culture liquor having a methanol concentration of 0.1 wt% or less was used as the seed yeast.

EXAMPLE 2

200 Milliliters of the same medium as in Example 1, except that 0.02 g of $MgSO_4.7H_2O$ was used, was charged into a 1,000-ml Erlenmeyer flask. Subsequently, a yeast *Saccharomyces metha-nonfoaws* T-80 (FERM P-1927) (MRRL Y-8026) was inoculated in the medium, and subjected to seed culture at 30° C. by use of a rotary shaker. As the result, the yeast propagated until the yeast concentration reached an optical density at 610 mµ of 2.2, and the said yeast concentration was maintained thereafter. The methanol concentration in the culture liquor decreased with growth of the yeast and with lapse of time, and was 0.32 wt% when the yeast concentration reached the said optical density at 610 mµ of 2.2. The yeast at this stage was used as a seed yeast, and was immediately inoculated into, and cultured in a 3-liter jar fermentor containing 1 liter of the same medium as in Example 1. At the time of inoculation, the methanol concentration in the culture liquor containing the seed yeast was measured to find that the aforesaid methanol concentration of 0.32 wt% was maintained. After 8 hours of growth induction period, the seed yeast began to propagate vigorously.

For comparison, the same cultivation as above was repeated, except that the yeast in the seed culture liquor having a methanol concentration of 0.05 wt% was used as the seed yeast. In this case, the growth induction period was 16 hours.

EXAMPLE 3

200 Milliliters of the same medium as in Example 1, except that 0.02 µg of biotin was used, was charged into a 1,000-ml Erlenmeyer flask. Subsequently, a yeast *Torulopsis methanofloat* A-86 (FERM P-1974) (NRRL Y-8028) was inoculated in the medium, and subjected to seed culture at 30° C. by use of a rotary shaker. As the result, the yeast propagated until the yeast concentration reached an optical density at 610 mµ of 1.6, and the said yeast concentration was maintained thereafter. The methanol concentration in the culture liquor decreased with growth of the yeast and with lapse of time, and was 0.49 wt% when the yeast concentration reached the said optical density at 610 mµ of 1.6. The yeast at this stage was used as a seed yeast, and was immediately inoculated into, and cultured in, a 3-liter jar fermentor containing 1 liter of the same medium as in Example 1. Immediately before inoculation, the methanol concentration in the culture liquor containing the seed yeast was measured to find that the aforesaid methanol concentration of 0.49 wt% was maintained. After 6 hours of growth induction period, the seed yeast began to propagate vigorously.

For comparison, the same cultivation as above was repeated, except that the yeast in the seed culture liquor having a methanol concentration of 0.06 wt% was used as the seed yeast. In this case, the growth induction period was 14 hours.

EXAMPLE 4

200 Milliliters of the same medium as in Example 1 was charged into a 1,000-ml Erlenmeyer flask. Subsequently, a yeast Candida N-17 (FERM P-426) (NRRL Y-8024) was inoculated in the medium, and subjected to seed culture at 30° C. by use of a rotary shaker. The methanol concentration in the culture liquor decreased with growth of the yeast and with lapse of time. When the methanol concentration became 0.2 wt%, the yeast in the culture liquor was used as a seed yeast. The seed yeast was immediately inoculated into, and cultured in, a 3-liter jar fermentor containing 1 liter of the same medium as in Example 1. At the time of inoculation, the methanol concentration in the culture liquor containing the seed yeast was measured to find that the aforesaid methanol concentration of 0.2 wt% was maintained. After 6 hours of growth induction period, the seed yeast began to propagate vigorously.

For comparison, the same cultivation as above was repeated, except that the yeast in the seed culture liquor having a methanol concentration of 0.002 wt% was used as the seed yeast. In this case, the growth induction period was 18 hours.

EXAMPLE 5

200 Milliliters of the same medium as in Example 1 was charged into a 1,000-ml. Erlenmeyer flask. Subsequently, a yeast Saccharomyces H-1 (FERM P-549) (NRRL Y-8027) was inoculated in the medium, and subjected to seed culture at 30° C. by use of a rotary shaker. The methanol concentration in the culture liquor decreased with growth of the yeast and with lapse of time. When the methanol concentration became 0.3 wt%, the yeast in the seed culture liquor was used as a seed yeast. The seed yeast was immediately inoculated into, and cultured in, a 3-liter jar fermentor containing 1 liter of the same medium as in Example 1. At the time of inoculation, the methanol concentration in the culture liquor containing the seed yeast was measured to find that the aforesaid methanol concentration of 0.3 wt% was maintained. After 5 hours of growth induction period, the seed yeast began to propagate vigorously.

For comparison, the same cultivation as above was repeated, except that the yeast in the seed culture liquor having a methanol concentration of 0.000 wt% was used as the seed yeast. In this case, the growth induction period was 16 hours.

EXAMPLE 6

200 Milliliters of the same medium as in Example 1 was charged into a 1,000-ml. Erlenmeyer flask. Subsequently, a yeast *Hansenula alcolica* UM-88 (FERM P-2065) (NRRL Y-8025) was inoculated in the medium and subjected to seed culture at 30° C. by use of a rotary shaker. The methanol concentration in the culture liquor decreased with growth of the yeast and with lapse of time. When the methanol concentration became 0.15 wt%, the yeast in the seed culture liquor was used as a seed yeast. The seed yeast was immediately inoculated into, and cultured in, a 3-liter jar fermentor containing 1 liter of the same medium as in Example 1. At the time of inoculation, the methanol concentration in the culture liquor containing the seed yeast was measured to find that the aforesaid methanol concentration of 0.15 wt% was maintained. After 7 hours of growth induction period, the seed yeast began to propagate vigorously.

For comparison, the same cultivation as above was repeated, except that the yeast in the seed culture liquor having a methanol concentration of 0.004 wt% was used as the seed yeast. In this case, the growth induction period was 18 hours.

EXAMPLE 7

*Saccharomyces metha-nonfoams* T-80 (FERM P-1927) (NRRL Y-8026) was inoculated in the same medium (500 ml) as in Example 1 in a 1,000 ml fermentor. Cultivation was conducted batch-wise at pH 4.5 and 28° C. When the microorganism grew and the methanol concentration in the culturing medium decreased to 0.05 wt%, the cultivation was changed to a continuous manner wherein the same medium as above was fed continuously, discharging the same amount of the medim as that fed. The yeast was cultured continuously for 7 hours of average residence time, and the methanol concentration in the culturing medium was 0.15% when the culture reached the stationary state. The yeast obtained was inoculated as a seed yeast to 15 liters of the same medium as Example 1 in a 30 liter jar fermentor. The methane concentration in the culturing medium containing the seed yeast at that time was still kept at 0.15 wt%. Vigorous growth was observed after 4 hours of growth induction period.

On the other hand, the methanol concentration in a culturing medium was 0.01 wt% and the stationary state was obtained, when a seed yeast is cultured continuously for about 10 hours of average residence time. This yeast was inoculated as a seed yeast in the same medium (15 liters) as Example 1 in a 30 liter jar fermentor. The yeast began to propagate vigorously after 15 hours of growth induction period.

What is claim is:

1. A process for shortening the growth induction period of methanol-utilizing yeasts which comprises preculturing a yeast capable of utilizing methanol in a seed culture medium containing methanol as a main carbon source in a concentration higher than 0.1 weight % and not more than 6 weight % and additionally containing nutrient nitrogen sources and inorganic compounds to obtain a seed yeast, inoculating the seed yeast into an aqueous nutrient fermentation medium containing methanol as a main carbon source, the methanol concentration in the seed culture liquor being within said range of higher than 0.1 weight % and not more than 6 weight % at the time of inoculation thereof into the fermentation medium, and cultivating the yeast in the fermentation medium in a continuous manner.

2. A process according to claim 1, wherein said seed culture medium contains in required amounts all of said nutrient nitrogen sources and inorganic compounds or other nutrient sources.

3. A process according to claim 1, wherein said seed culture medium contains in an insufficient amount at least one of said nutrient nitrogen sources and inorganic compounds or other nutrient sources except the methanol.

4. A process according to claim 1, wherein the yeast is selected from the group consisting of *Candida alcomigas, Saccharomyces metha-nonfoams, Torulopis Methanofloat, Candida N-17, Saccharomyces H-1 and Hansenula alcolica*.

5. A process according to claim 1, wherein the yeast is *Saccharomyces metha-nonfoams* NRRL Y-8026.

6. A process according to claim 1, wherein the yeast is Candida N-17 NRRL Y-8024.

7. A process according to claim 1, wherein the yeast is Saccharomyces H-1 NRRL Y-8027.

8. A process according to claim 1, wherein the yeast is *Hansenula alcolica* NRRL Y-8025.

9. A process for shortening the growth induction period of the microorganism *Candida alcomigas* NRRL Y-8023 which comprises pre-culturing said microorganism in a seed culture medium containing methanol as a main carbon source in a concentration higher than 0.1 weight % and not more than 6 weight % and additionally containing nutrient nitrogen sources and inorganic compounds to obtain a seed yeast, and then inoculating and cultivating said seed yeast in an aqueous nutrient fermentation medium containing methanol as a main carbon source, the methanol concentration in the seed culture liquor being within said range of higher than 0.1 weight % and not more than 6 weight % at the time of inoculation thereof into the fermentation medium.

10. A process for shortening the growth induction period of the microorganism *Torulopsis methanofloat* NRRL Y-8028 which comprises pre-culturing said microorganism in a seed culture medium containing methanol as a main carbon source in a concentration higher than 0.1 weight % and not more than 6 weight % and additionally containing nutrient nitrogen sources and inorganic compounds to obtain a seed yeast, and then inoculating and cultivating said seed yeast in an aqueous nutrient fermentation medium containing methanol as a main carbon source, the methanol concentration in the seed culture liquor being within said range of higher than 0.1 weight % and not more than 6 weight % at the time of inoculation thereof into the fermentation medium.

* * * * *

UNITED STATES PATENT AND TRADEMARK OFFICE
CERTIFICATE OF CORRECTION

PATENT NO. : 4,229,543
DATED : October 21, 1980
INVENTOR(S) : Tonomura et al

It is certified that error appears in the above—identified patent and that said Letters Patent is hereby corrected as shown below:

In the heading "[73] Assignees":

The Assignees should read as follows:

Agency of Industrial Science and Technology, Ministry of International Trade and Industry and Mitsubishi Gas Chemical Company, Inc., both of Tokyo, Japan Signed and Sealed this Tenth Day of March 1981

[SEAL]

Attest:

Attesting Officer

RENE D. TEGTMEYER

Acting Commissioner of Patents and Trademarks